(12) United States Patent
Siemers

(10) Patent No.: US 6,394,453 B1
(45) Date of Patent: *May 28, 2002

(54) PSYCHO-SOCIAL GAME THAT MEASURES EMOTIONAL DISTANCE BETWEEN PLAYERS' RESPONSES

(76) Inventor: Donna L. Siemers, 11125 E. Day Mt. Spokane Rd., Mead, WA (US) 99021

( * ) Notice: Subject to any disclaimer, the term of this patent is extended or adjusted under 35 U.S.C. 154(b) by 0 days.

This patent is subject to a terminal disclaimer.

(21) Appl. No.: 09/515,573

(22) Filed: Feb. 29, 2000

Related U.S. Application Data

(63) Continuation-in-part of application No. 08/584,158, filed on Jan. 11, 1996, now Pat. No. 6,029,975, which is a continuation-in-part of application No. 08/176,802, filed on Jan. 3, 1994, now abandoned.

(51) Int. Cl.[7] ............................................... A63F 3/02
(52) U.S. Cl. .................................. 273/242; 273/236
(58) Field of Search ......................... 273/242, 243, 273/244, 248, 249, 236; 700/9

(56) References Cited

U.S. PATENT DOCUMENTS

| | | | |
|---|---|---|---|
| 3,764,135 A | 10/1973 | Madison | 273/1 R |
| 4,013,294 A | * 3/1977 | Smeda et al. | |
| 4,124,214 A | * 11/1978 | Pavis | |
| 4,216,594 A | * 8/1980 | Farley et al. | |
| 4,216,971 A | * 8/1980 | Lyke | |
| 4,230,320 A | * 10/1980 | Crew | |
| 4,230,321 A | 10/1980 | Smith | 273/308 |
| 4,234,185 A | 11/1980 | Alsip | 273/243 |
| 4,244,577 A | 1/1981 | Poulos | 273/236 |
| 4,273,337 A | * 6/1981 | Carrera et al. | |
| 4,344,625 A | 8/1982 | Frudakis | 273/242 |
| 4,354,844 A | 10/1982 | Ickinger | 434/237 |
| 4,372,559 A | * 2/1983 | Summers | |
| 4,508,353 A | 4/1985 | Meyer et al. | 273/313 |
| 4,618,146 A | 10/1986 | Yoshida et al. | 273/1 E |

(List continued on next page.)

FOREIGN PATENT DOCUMENTS

| | | | |
|---|---|---|---|
| DE | 3800221 | * | 7/1989 |
| GB | 2 215 222 A | | 9/1989 |

OTHER PUBLICATIONS

Paper on "A Set of Categories for the Analysis of Small Group Interaction", Robert F. Bales, American Sociological Review, pp. 257–263.

Primary Examiner—Benjamin H. Layno
Assistant Examiner—Vishu K. Mendiratta
(74) Attorney, Agent, or Firm—R. Reams Goodloe, Jr.

(57) ABSTRACT

A method for determining the emotional distance between individuals. A method of evaluating the emotional distance between individuals is described by use of a computerized database or game process wherein the players are provided with a number of hypothetical human interaction situations, offered a set of possible responses for each situation, and are also given an opportunity to create unique responses. A coding system is provided for prepared responses, and a response coding method is provided for determining the behavior category of the player's response. Players each set forth their response behavior code on the game board, or by remote input to a database. The majority response is established, and the distance of each individual from the majority is determined. The method includes a scorekeeping system for determining the emotional distance between players responses. The method includes providing to the player a game score for the player's response selection wherein the value of the game score is based upon the distance between the players preferred response and the response of the majority, in game(i) and the player's ability to take the role of the other in game (ii) and game (iii). The winner of game (i) is the player who learns to code behavior well enough to negotiate better social relationships. The winner of game (ii) and game (iii) is the person who is best able to take the role of the other. Further a diplomacy teaching exercise is provided to enable players to measure their ability to provide diplomatic responses to various situations.

55 Claims, 11 Drawing Sheets

U.S. PATENT DOCUMENTS

| | | |
|---|---|---|
| 4,741,539 A | 5/1988 | Sutton et al. .............. 273/275 |
| 4,813,681 A | 3/1989 | Volpert ..................... 273/271 |
| 4,846,479 A | 7/1989 | Hanley ..................... 273/236 |
| 4,893,819 A * | 1/1990 | Wright |
| 4,909,740 A | 3/1990 | Rankin ..................... 434/238 |
| 5,020,804 A | 6/1991 | Weedman ................. 273/249 |
| 5,037,305 A | 8/1991 | Aleck ....................... 434/262 |
| 5,054,775 A | 10/1991 | Banks et al. .............. 273/431 |
| 5,108,115 A | 4/1992 | Berman et al. ........... 273/439 |
| 5,178,544 A | 1/1993 | Aleck ....................... 434/262 |
| 5,950,200 A * | 9/1999 | Sudai et al. |
| 5,963,951 A * | 10/1999 | Collons |
| 6,061,681 A * | 5/2000 | Collins |

* cited by examiner

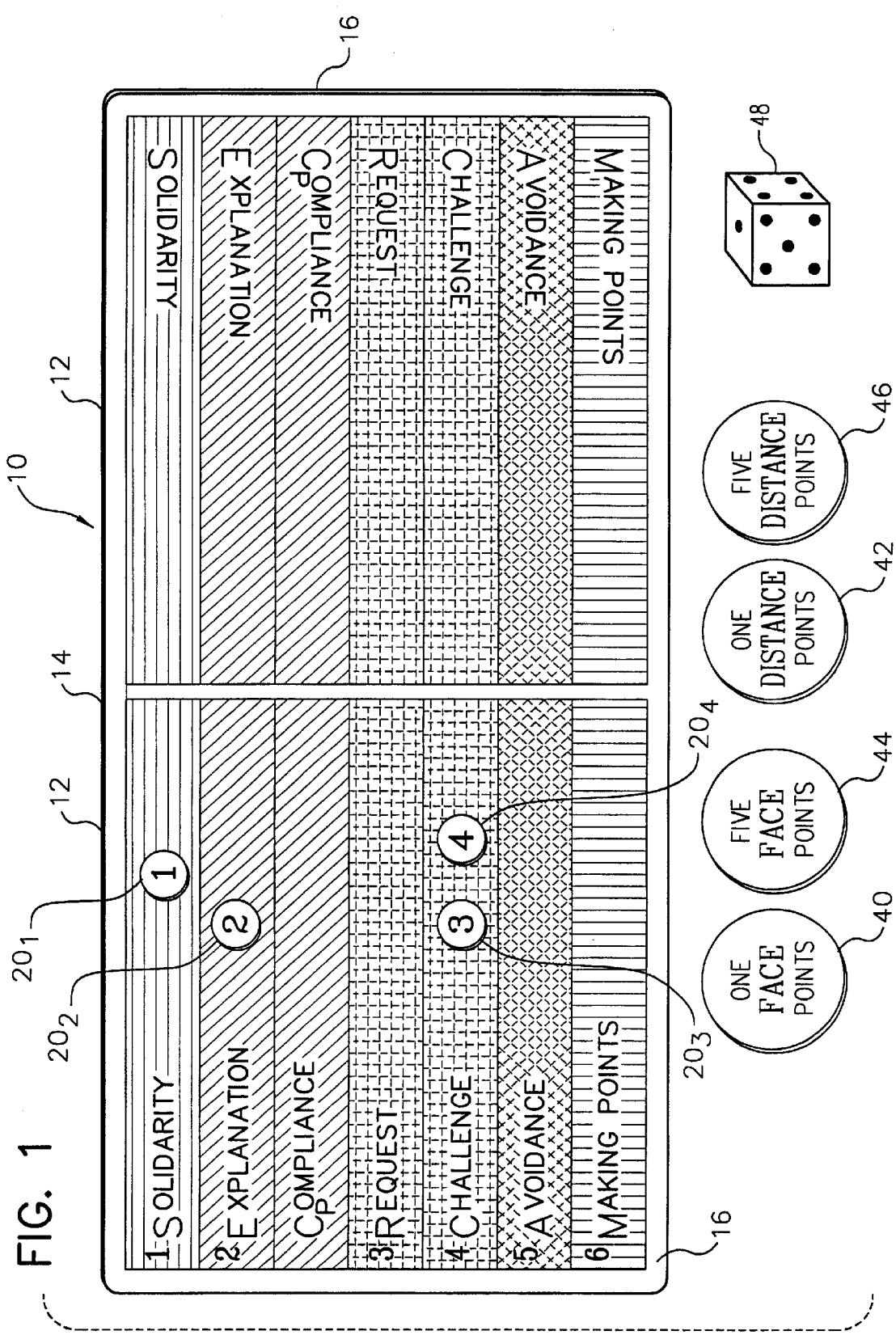

FIG. 6A

SCORE SHEET—Game (i)

NAME _____ DATE __/__/20__

SOCIAL CHARACTERISTICS: PLEASE WRITE IN YOUR OCCUPATION AND CHECK YOUR SEX, AGE, INCOME, RACE, MARITAL STATUS AND HIGHEST LEVEL OF EDUCATION:

OCCUPATION:                                 SEX: ☐ MALE ☐ FEMALE

AGE:     UNDER 25☐   25–34☐   35–44☐   45–54☐   55–64☐   65–74☐   75+☐

INCOME:    LESS THAN $10,000☐    $10,000–19,999☐    $20,000–34,999☐
              $35,000–59,999☐    $60,000–70,000☐    $80,000+☐

RACE:    CAUCASIAN☐ HISPANIC☐ ASIAN☐ NATIVE AMERICAN☐ BLACK☐
        OTHER: ☐

MARITAL STATUS:    NEVER☐ MARRIED☐ SEPARATED☐ DIVORCED☐ WIDOWED☐
                   OTHER☐

EDUCATION:    GRADE SCHOOL☐ HIGH SCHOOL☐ SOME COLLEGE☐ B.A.☐
               MA.☐ PhD.☐

| CARD | CODE | RESPONSE | DISTANCE POINTS | FACE POINTS |
|---|---|---|---|---|
| 1 | | | | |
| 2 | | | | |
| 3 | | | | |
| 4 | | | | |
| 5 | | | | |
| 6 | | | | |
| 7 | | | | |
| 8 | | | | |
| 9 | | | | |
| 10 | | | | |
| 11 | | | | |
| 12 | | | | |

FIG. 6B

| CARD | CODE | RESPONSE | DISTANCE POINTS | FACE POINTS |
|---|---|---|---|---|
| 13 | | | | |
| 14 | | | | |
| 15 | | | | |
| 16 | | | | |
| 17 | | | | |
| 18 | | | | |
| 19 | | | | |
| 20 | | | | |
| 21 | | | | |
| 22 | | | | |
| 23 | | | | |
| 24 | | | | |
| 25 | | | | |
| TOTAL | | | | |

1. FACE POINTS INDICATE THE NUMBER OF TIMES THAT A PLAYER TOOK THE ROLE OF MAJORITY, DURING THE GAME.

2. DISTANCE POINTS MEASURE THE DIFFERENCE IN EMOTIONAL INTENSITY BETWEEN THE RESPONSES OF THE MAJORITY AND THE RESPONSES OF THE INDIVIDUAL PLAYER.

3. WINNING IS TO HAVE YOUR DISTANCE POINT SCORE REPRESENT WHO YOU THINK YOU ARE AND WHAT YOU DO IN RELATIONSHIP TO THE OTHER GAME PLAYERS. IF YOU ARE PLAYING THE GAME WITH A GROUP OF INDIVIDUALS WHOSE PERSPECTIVES YOU DO NOT APPROVE OF, YOU MAY DECIDE THAT DISTANCE BETWEEN THEIR PERSPECTIVES AND YOURS IS OKAY. THE EXTENT TO WHICH THE PLAYER IS A WINNER IS THE DECISION OF THE PLAYER.

4. IF YOU WISH TO LEARN TO NEGOTIATE THE EMOTIONAL DISTANCE BETWEEN YOU AND OTHERS, YOU MAY WISH TO PLAY "DIPLOMACY." Select your task(s) for playing Diplomacy with the same group of players according to the situations for which you have two or more distance points:

| TASK SELECTION CHART | | | | | |
|---|---|---|---|---|---|
| SITUATIONS | 1-4 | 5-9 | 10-14 | 15-19 | 20-25 |
| TASK | #1 | #2 | #3 | #4 | #5 |

FIG. 7

| # | CARD CODE | RESPONSE | FACE POINTS | GUIDE DISTANCE POINTS | ROLE RESPONSE CODES | ROLE DISTANCE POINTS |
|---|---|---|---|---|---|---|
| 1 | | | | | | |
| 2 | | | | | | |
| 3 | | | | | | |
| 4 | | | | | | |
| 5 | | | | | | |
| 6 | | | | | | |
| 7 | | | | | | |
| 8 | | | | | | |
| 9 | | | | | | |
| 10 | | | | | | |
| 11 | | | | | | |
| 12 | | | | | | |
| 13 | | | | | | |
| 14 | | | | | | |
| 15 | | | | | | |
| 16 | | | | | | |
| 17 | | | | | | |
| 18 | | | | | | |
| 19 | | | | | | |
| 20 | | | | | | |
| 21 | | | | | | |
| 22 | | | | | | |
| 23 | | | | | | |
| 24 | | | | | | |
| 25 | | | | | | |
| TOTAL | | | | | | |

SCORE SHEET—Game (ii)

NAME _____ DATE __/__/20__

FIG. 8

| | SCORE SHEET–Game (iii) | | | |
|---|---|---|---|---|
| NAME _____ DATE __/__/20__ | | | | |

| CARD CODE | RESPONSE | | DISTANCE POINTS | FACE POINTS |
|---|---|---|---|---|
| 1 | | | | |
| 2 | | | | |
| 3 | | | | |
| 4 | | | | |
| 5 | | | | |
| 6 | | | | |
| 7 | | | | |
| 8 | | | | |
| 9 | | | | |
| 10 | | | | |
| 11 | | | | |
| 12 | | | | |
| 13 | | | | |
| 14 | | | | |
| 15 | | | | |
| 16 | | | | |
| 17 | | | | |
| 18 | | | | |
| 19 | | | | |
| 20 | | | | |
| 21 | | | | |
| 22 | | | | |
| 23 | | | | |
| 24 | | | | |
| 25 | | | | |
| TOTAL | | | | |

FIG. 9A

SCORE SHEET – Diplomacy

NAME _____ DATE ___/___/20___

| RESPONSES | PLAYERS | | | | MEDIAN | DISTANCE |
|---|---|---|---|---|---|---|
| | 1 | 2 | 3 | 4 | POINTS | POINTS |
| 1 | | | | | | |
| 2 | | | | | | |
| 3 | | | | | | |
| 4 | | | | | | |
| 5 | | | | | | |
| 6 | | | | | | |
| 7 | | | | | | |
| 8 | | | | | | |
| 9 | | | | | | |
| 10 | | | | | | |
| 11 | | | | | | |
| 12 | | | | | | |
| 13 | | | | | | |
| 14 | | | | | | |
| 15 | | | | | | |
| 16 | | | | | | |
| 17 | | | | | | |

FIG. 9B

SCORE SHEET-Diplomacy
NAME _____ DATE ___/___/20___

| RESPONSES | PLAYERS | | | | MEDIAN POINTS | DISTANCE POINTS |
|---|---|---|---|---|---|---|
| | 1 | 2 | 3 | 4 | | |
| 18 | | | | | | |
| 19 | | | | | | |
| 20 | | | | | | |
| 21 | | | | | | |
| 22 | | | | | | |
| 23 | | | | | | |
| 24 | | | | | | |
| 25 | | | | | | |
| 26 | | | | | | |
| 27 | | | | | | |
| 28 | | | | | | |
| 29 | | | | | | |
| 30 | | | | | | |
| 31 | | | | | | |
| 32 | | | | | | |
| 33 | | | | | | |
| 34 | | | | | | |
| TOTALS | | | | | | |

FIG. 11

MENU

Soul Mate: Who could be my soul mate? What are the issues that will cause conflict in our relationship? How can we learn the skills needed to negotiate a closer relationship. How can we prevent our relationship from deteriorating.?

Work Group Selection: Which people could be most productive working together to complete to type of task that I need completed? Why are some people more productive when working together on a particular task than others?

Student-Faculty-Parent Relations: Are there emotional distances between students, faculty and parents that could be negotiated? What are the issues that cause the emotional distances to emerge? Why do these issues cause conflict? What kind of intervention program can be used to teach people how to negotiate the emotional distances in their relationships?

Family Therapy: What are the issues that cause conflict in our family relations? Why do these issues cause conflict? How can my family learn the skills needed to negotiate closer relationships? How can we prevent our relationship from deteriorating?

Prenuptial Counseling: What are the issues that will cause conflict between us? Why do these issues cause conflict? How can we learn to negotiate emotional distance in this relationship? How can we prevent our relationship from deteriorating?

Hung Jury: How can I select a jury that will not be able to come to a consensus concerning a particular trial? How can I learn the rules that I can use to select the type of jury that I want?

Swing Vote: What percentage of the people in this database: 1) are for a particular issue; 2) against the issue; 3) need more information before deciding how to vote on the issue; 4) are closer to being for the issue than against it; and 5) are more against the issue than being for it?

PSYCHO-SOCIAL GAME THAT MEASURES EMOTIONAL DISTANCE BETWEEN PLAYERS' RESPONSES

This patent application is a continuation-in-part of U.S. patent application Ser. No. 08/584,158, filed Jan. 11, 1996, now U.S. Pat. No. 6,029,975, which was a continuation of U.S. patent application Ser. No. 08/176,802, filed Jan. 3, 1994, now abandoned.

A portion of the disclosure of this patent document contains material which is subject to copyright protection. The owner has no objection to the facsimile reproduction by anyone of the patent document or the patent disclosure, as it appears in the Patent and Trademark Office patent file or records, but otherwise reserves all copyright rights whatsoever.

TECHNICAL FIELD

This invention relates to methods for measurement of the emotional distance between individuals in given situations of human interaction, and to games which utilize such methods.

BACKGROUND

Sociologists and psychologists have long recognized that a relationship exists between socially-deviant behavior and the lack of roletaking ability of the individuals exhibiting such behavior. More particularly, psychologists have long recognized that child development, both intellectually and emotionally, is in part dependent upon the roletaking capacities of their parents and teachers. Further, it has been recognized that the satisfactory and successful conduct of affairs in the adult world, especially in the area of communication and negotiation, is facilitated where the participants in a particular affair have the ability to take on the role of the other participants and to respond in such situations on the same emotional level as the other participants.

The study of roletaking, particularly with a view towards the establishment of systematic methods for development and measurement of roletaking ability, has thus been an important concern of sociological and psychological research. One method for such measurement that to some remote extent resembles the method disclosed and claimed herein is described in U.S. Pat. No. 3,764,135, issued Oct. 9, 1973, to Madison and titled "Empathy Game." That game operationalizes empathy as roletaking ability, and yields an empathy score that is a composite of the number of times that both members of a dyad are able to assume a given role and then select the same response from a given number of responses, for a given number of situations. Madison's work provides a method for testing the same individual against a number of other individuals, sequentially. That is, one's capability concerning roletaking behavior may vary from one partner to the another, and Madison shows how that variance can be measured. Madison's work also teaches roletaking in that it offers an opportunity for the same two individuals to replay the game, and to make different response selections during such replay, in order to achieve a more desirable outcome. However, Madison's approach is limited to measurement of the cumulative number of roletaking instances between two players. His method is also limited to the predetermined role choice options provided by the game. Significantly, Madison's game makes no provision for estimating the varying amounts of emotional distance between players' response choices.

While the just mentioned efforts of Madison are suggestive of the fact that (a) measurement, and (b) stimulation of roletaking ability are both matters of importance, substantial progress in this field has heretofore been limited due to the lack of adequate methodology in the field.

Therefore, with respect to measurement of emotional distance between individuals, there remains a great, unresolved need for a reliable methodology which can:
  (i) measure the emotional distance between differing responses when individuals do not select the same response to a given situation;
  (ii) enable individuals to create and interpret their own responses when there are no predetermined response choices available;
  (iii) identify the issues over which individuals experience emotional distance;
  (iv) utilize skills learned from use of the method to interpret and modify relationships in everyday life; and which ideally, can (v) measure the emotional distance between the selected responses of more than two individuals at the same time.

Particularly in Asian societies, such as in Japan, the ability to respond in a socially acceptable manner, not emotionally distant from others involved, is an important social and business skill. For example, in many business situations, it may be the potential "loss of face" and not the immediate business economic consequences which are paramount in business decision making. Understanding the motivating forces behind such behavior in business decisions which maintain "face" or result in "loss of face" would be of particular advantage for businessmen dealing with such cultures.

Because the linkage between (i) the way that a particular behavior functions, (ii) the level of emotional distance that such behavior expresses, and (iii) the differences in interactants' perspectives on such behavior, given the same situation, has not heretofore been described, scientists and others have encountered serious difficulties in attempting to measure emotional distance between individuals as it relates to roletaking. Still more difficult has been the stimulation and development of roletaking ability in individuals. This problem has been exacerbated given the lack of any systematic method for developing such roletaking ability. Further, there exists a need for a system which enables the development of roletaking ability in a variety of settings.

In summary, with respect to roletaking, there currently exists in the art a great need for new and improved methods for:
  1) measuring roletaking ability;
  2) measuring the emotional distance between interactants' responses to a given situation when the parties do not take the role of the other;
  3) identifying those issues that prevent particular combinations of persons from putting themselves in the role of others; and
  4) providing strategies that interactants can use to improve their roletaking abilities in every-day life.

In addition, a critical need currently exists in the field of psychotherapy for a method which enables the development of roletaking ability. Moreover, it is likely that most social relationships could be significantly improved by increasing the roletaking abilities of the participants. Finally, for persons desiring to increase their own roletaking capabilities, or desiring to encourage roletaking development in others, there clearly exists a need for simple methods for recognizing, measuring, understanding, stimulating and developing such roletaking ability.

SUMMARY

I have invented, and disclose herein, a novel method for evaluation of the emotional distance between individuals.

My method recognizes that various forms of human social behavior can be described by use of discrete functional categories. Most simply, behavior can be described by use of two categories, IN-FACE or OUT-OF FACE behavior. However, in my method, I have found that it is more useful to use three basic categories for such description; those categories are (i) SOLIDARITY, (ii) NEGOTIATION, and (iii) NON-COMPLIANT behavior. With respect to the above described basic two behavior category system, IN-FACE behavior includes SOLIDARITY, and all other behavior categories are considered OUT-OF-FACE.

The three basic behavior categories set forth in the preceding paragraph can be broken down into further defined sub-categories. Therefore, in one exemplary embodiment of my method, NEGOTIATION can be further defined as (a) an EXPLANATION, (b) COMPLIANCE, or (c) a REQUEST. The REQUEST category includes commands and demands for specific behaviors as well as inquiries for further information. Also in that embodiment, NON-COMPLIANT behavior can be further defined as (a) DISAGREEMENT (or CHALLENGE), (b) AVOIDANCE, or (c) MAKING POINTS (or PUT-DOWN).

I have found that it is most useful to utilize seven functional categories and sub-categories (hereinafter "categories"), as they provide a convenient basis for the evaluation of behavior. Each of these seven categories of behavior expresses a different level of emotional distance between interactants. The emotional distance between individuals relates to the differences between their perspectives concerning the situations which they are faced with. These seven categories are (i) SOLIDARITY, (ii) EXPLANATION, (iii) COMPLIANCE, (iv) REQUEST, (v) CHALLENGE, (vi) AVOIDANCE, and (vii) MAKING POINTS.

An ordinal variable of emotional distance can be formed by arranging the seven above named categories of behavior according to the amount of emotional distance that each function expresses during social interaction.

SOLIDARITY includes AGREEMENT, and APPROVAL, which indicate no emotional distance between interactants.

NEGOTIATION includes behavior that functions in one of three ways:

First, polite EXPLANATION, that neither agrees with nor disagrees with the other, expresses a slight emotional distance between interactants. Explanation is not necessary when people are in agreement.

Second, COMPLIANT behavior is a polite response to a request and expresses slightly more emotional distance than explanation. When someone makes a request, compliance is expected.

Third, when a person REQUESTS a response from the other, his or her behavior expresses slightly more emotional distance than compliant behavior.

NON-COMPLIANT behavior includes behavior that functions in one of three ways:

First, an expression of DISAGREEMENT shows more emotional distance than an expression amounting to a REQUEST.

Second, AVOIDANCE, which is tinged with anger, indicates more emotional distance than disagreement.

Third, MAKING POINTS behavior, that is behavior which tends to be rude or PUT someone DOWN, is the most emotionally distant behavior of all.

Thus, by identifying a particular behavior, and categorizing that particular behavior according to function, such as within the above described seven categories, the emotional closeness or distance between individuals can be estimated, based on particular preferred responses by the individuals.

I have found that it is useful to utilize (a) three board games, (b) a task completion activity, and (c) an Internet based business, to embody the present invention. Each of these methods of employing my invention provides a convenient method for the evaluation of human behavior. Each of the three board games evaluates a different aspect of the emotional distance between players, as such emotional distance relates to a variety of social situations. I have named the board games (i) BE YOURSELF™ (this evaluates the emotional distance between players as it relates to the differences in players' perspectives concerning a variety of social situations), (ii) BE THE OTHER™ (this game evaluates the emotional distance between a player's ability to take the role of the other and the demonstrated role of the other), and (iii) CREATE THE OTHER™ (this game evaluates the emotional distance between each player's effort to create the role of a hypothetical other and his ability to do so, as viewed by the other players).

Game (i) specifically the BE YOURSELF™ game, involves a method of playing a game with two or more players wherein the players are provided with a number of hypothetical situations and are offered a set of possible responses to the situation. Players may also be given an opportunity to create unique responses, and in such situations, are provided with a set of rules for categorizing the responses by behavior type, so that the preferred responses can be evaluated in terms of the emotional distance between the various responses. The method used in this game includes providing to each player a score for the player's response selections wherein the total value of the game score is based upon the differences (i.e., the emotional distance) between the players' perspectives. Uniquely, the extent to which a player is a winner is the decision of the player. It is up to each individual player to decide if the distance is good or bad. If you are playing the game with other players whose perspectives you do not approve of you may decide that a large distance between your perspective and their perspectives is O.K. A "winning" score is thus a score wherein your distance point score represents who you think you are, and what you do, in relationship to the other game players.

Game (ii) the BE THE OTHER™ game, evaluates the emotional distance between a players' ability to take the role of the other, and the demonstrated role of the other. This game involves a method of playing a game with one or more sets of players (two players in each set of players) wherein the players are provided with the same hypothetical situations as offered within game (i). Specifically, the players are offered a set of possible responses (and may also be given an opportunity to create unique responses and provided with a set of rules for categorizing such responses by behavior type), so that the preferred responses can be evaluated in terms of the emotional distance between the actual responses of one player and the roletaking responses of the other player. The method used in this game includes providing to each player a score for the player's roletaking response selections wherein the total value of the game score is based upon the difference between one player's actual response score and the other player's roletaking response score. The winner is this BE THE OTHER™ game is the player whose roletaking response choices indicate the least total emotional distance from the actual response choices of the other player, as recorded during the game.

Game(iii) my CREATE THE OTHER™ game, evaluates the emotional distance between each player's effort to create the role of a hypothetical individual, and the player's own ability to create such a hypothetical individual, as viewed by the other players. Game (iii) involves a method of playing a game with two or more players wherein the players are provided with a number of hypothetical situations, are given an opportunity to roll a single die, and are asked to create a unique response in the category indicated by the die. Players are provided with a set of rules for categorizing responses by behavior type, so that responses can be evaluated in terms of the emotional distance between the response required by the roll of the die and the response created by the player, as viewed by the other (non die-rolling) players.

Diplomacy is a task completion activity which evaluates the emotional distance between each participant's responses and the diplomatic response categories (i.e., SOLIDARITY and NEGOTIATION). Diplomacy as practiced in the various methods of the present invention involves providing participants with a task to complete, the content of which is based on either (a) the most distancing issues of game(i), as indicated by the game scores, or (b) a recommendation from database E or F (see below). Instructions include the requirement (a) to use only diplomatic category responses when communicating with one another, and, (b) to write all responses on a score sheet (see FIG. 7). When finished working on the task, participants exchange response sheets so that each participant codes each of the other participant's responses using the set of rules provided for categorizing the responses by behavior type. Response sheets are then returned to their owners. The response sheet owner then enters the median score and the distance score (the distance score is equal to the emotional distance that is greater than the REQUEST category of behavior). The method used in this activity includes providing to each participant a score for his actual responses wherein the total value of the score is based upon the distance between the value scored for the player's actual responses and the value which would have been scored for a response in a diplomatic response category. The winner of this activity is the participant whose responses indicate the least total emotional distance from the diplomatic response categories (as viewed by the other participants).

Another embodiment of the present invention is an Internet based business that includes, but is not limited to use of one or more integrated databases that include a plurality of data from one or more of the following database categories:

(A) Soul Mate (SM),
(B) Student-Faculty-Parent Relations (SFPR),
(C) Hung Jury (HJ),
(D) Work Group Selection (WGS),
(E) Family Therapy (FT),
(F) Prenuptial Counseling (PC), and
(G) Swing Vote.

A description of the various data categories follows:

A. Soul Mate™

The Soul Mate™ portion of the database collects a client's demographic and response data to create a personal data profile. This provides an opportunity for each client to enter a description of the mate desired. A sort of single's response data is conducted to identify participants whose description matches the description entered by the client, and importantly, whose perspective shows the least emotional distance from the client. This Soul Mate™ database provides a method for identifying participants whose perspectives are the most similar, by providing participants with a series of hypothetical situations and a set of possible responses that have been categorized so that the preferred responses can be evaluated in terms of the emotional distance between participants' perspectives. The method used in creation of this database includes providing each participant with the opportunity to become a database member, to enter his/her data, to search the database for suitable individuals who share his/her perspective, and provide an output of contact information (preferably in the form of a printout) as well as an analysis of the prospective relationships in terms of emotional distance/closeness.

B. Student-Faculty-Parent Relations™

The Student-Faculty-Parent Relations™ (SFPR) portion of the database collects demographic and response data from students, faculty and parents to identify participants whose perspectives are the most emotionally distant, to identify and suggest intervention activities. The SFPR, database creation method involves identifying student participants whose perspectives exhibit (1) the most emotional distance between themselves and other students, (2) between themselves and faculty, and, (3) between themselves and their parents. This is accomplished by providing database participants with a series of hypothetical situations and a set of possible responses that have been categorized so that the preferred responses can be evaluated in terms of the emotional distance between participants' perspectives. The method used in this aspect of the database includes providing to each participant the opportunity to enter his data. Faculty members (or others) then search the database to identify students with the most isolated perspectives, (i.e., the greatest emotional distance). An output (preferably in the form of a printout) containing an analysis of these students' relationships with (1) other students, (2) parents, and, (3) faculty, is provided, and appropriate intervention activities are suggested.

C. Hung Jury™

The Hung Jury™ (HJ) portion of the database program collects demographic and jury member response data and sorts jury member response data to identify jury members who would not be able to reach a consensus concerning a particular trial. The Hung Jury™ database creation method involves identifying jury members who would not be able to reach a consensus concerning a particular trial matter by providing each jury member with a series of hypothetical situations and a set of possible responses that have been categorized, so that the preferred responses can be evaluated in terms of the emotional distance between potential jury members. The resulting data that shows emotional distance between jury member profiles provides an analysis of the composition of the desired jury.

D. Work Group Selection™

The Work Group Selection™ (WGS) portion of the database provides a method to collect and evaluate demographic data and employee response data. The employee data is sorted to identify a group of individuals who could most effectively work together on a particular task. The Work Group Selection™ database creation method involves identifying work group members who could most effectively complete a particular task by providing employees with a series of hypothetical situations and a set of possible responses, so that the preferred responses can be evaluated in terms of the emotional distance between work group members, with regard to the task at hand. The output of the WGS™ evaluation method involves providing an output, (preferably in the form of a printout), containing an analysis of the composition of the desired work groups and an estimate of group productivity, given a particular type of task.

E. Family Therapy™

The Family Therapy™ portion of the database provides a method for collection of demographic and family response data, and then compares family response data to identify issues that do or will produce conflict in family relationships. The FT™ portion of the database also provides a method for identifying issues with respect to which various family members' perspectives differ. This is accomplished by providing each family member with a series of hypothetical situations and a set of possible responses so that the preferred responses can be evaluated in terms of the emotional distance between the various family members with regard to particular situations. Family members will also be given an opportunity to create unique responses and provided with a set of rules for categorizing the responses by behavior type. The method used with the FT™ portion of the database provides an output, (preferably in the form of a printout), with an analysis of the distancing issues in the family's relationships, as well as suggested activities for negotiating closer relationships.

F. Prenuptial Counseling™

The Prenuptial Counseling™ portion of the database provides a method for collection of demographic and response data from each member of a couple undergoing evaluation and counseling. The method then compares the couple's data, each to the other, to identify issues that do or will produce conflict in the couple's relationship. The PC™ portion of the database involves a method of identifying issues with respect to which the perspectives of individual members of a couple differ. This is done by providing each member of the couple with a series of hypothetical situations and a set of possible responses so that the preferred responses can be evaluated in terms of the emotional distance between the two individuals, with regard to particular situations. Each member of the couple will also be given an opportunity to create unique responses, and provided with a set of rules for categorizing the responses by behavior type. The PC™ portion of the database, and my method for analysis and use of the data gathered, provides an output (preferably in the form of a printout analysis) of the distancing issues in the couple's relationship, as well as suggested activities for making decisions about the future of their relationship.

(G) The Swing Vote

The Swing Vote portion of the database and my method for analysis and use of the data gathered provides an output analysis (preferably in the form of a printout or screen display) of the attitudes of all members of the database, concerning specific issues, by geographic area.

OBJECTS, ADVANTAGES, AND NOVEL FEATURES

From the foregoing, it will be evident to the reader that a primary object of the present invention resides in the provision of a novel, improved method for measuring the emotional distances between individuals in a given human interaction situation.

A related and important object of the present invention is to provide an improved game process for measuring the emotional distance between players' responses.

It is a feature of the present invention that descriptive, discrete, and categorically complete behavior types are established in order to create a methodology for measurement of the emotional distance between individuals is established.

It is an important advantage of the present invention that a discrete value scale is provided to distinguish between behavior type categories, thus enabling an easy method of measurement of emotional distance between individuals.

Another object of the present invention is to provide a method for evaluating and predicting the probable proportions of non-compliant behavior for particular combinations of persons who will be asked to work together on specific tasks.

A related object similar to the just mentioned object is to provide a game process that produces ratings of players' performances that can be reliably used for prediction of the probable proportions of non-compliant behavior for particular combinations of persons who will be asked to work together on specific tasks.

It is a feature of the present invention that the probability of non-compliant behavior can be quickly and easily evaluated by use of the game process provided.

A unique advantage of the present invention is that it provides an easily implemented method for prediction of the likely success of industrial project teams, based on the interpersonal behavior of the participants, and more specifically, based upon the emotional distance between the individuals involved with respect to specific issues.

Another object of the present invention is to provide a game process that can be used for teaching social interaction, both in education and in industry, and to students and professionals alike.

Another object of the present invention is to provide an improved, entertaining game process for measuring one or more players' roletaking ability.

Yet another object of the present invention is to provide a game process that produces data that can be used by researchers to learn more about social interaction.

A further object of the present invention is to provide a game process that produces ratings of a player's performance which are reasonably accurate.

A still further object of the present invention is to provide a game process in which skills learned by players can be used to improve their social and business relationships in their everyday lives.

An important advantage of the game provided by the present invention is that it is fun and entertaining to play, thus facilitating the learning process.

Yet another object of the present invention is that it will produce a database that can be used by politicians to evaluate swing vote.

Still another object of the present invention is that it will produce a database that can be used by school administrators to evaluate students at risk for committing terrorist acts.

A unique advantage of the present invention is that it provides an easily implemented method for identifying the issues over which non-compliant behavior can be predicted.

Other important objects, features, and additional advantages of the invention will be apparent to the reader from the foregoing and the appended claims and as the ensuing detailed description and discussion of the invention proceeds in conjunction with the accompanying drawing.

BRIEF DESCRIPTION OF THE DRAWINGS

In the drawing:

FIG. 1 depicts an embodiment of the game board and game pieces.

FIG. 6A provides the obverse side of a scoring sheet.

FIG. 6B provides the reverse side of a scoring sheet.

FIG. 7 provides a scoring sheet.

FIG. 8 provides a scoring sheet.

FIG. 9A provides the obverse side of a scoring sheet.

FIG. 9B provides the reverse side of a scoring sheet.

FIG. 11 provides a menu for a database, and in particular, exemplary of a menu for a computer manipulated database.

DETAILED DESCRIPTION

Figure 3:
FIG. 3 depicts the obverse side of a game card.

For the purpose of promoting an understanding of the principles of the invention, reference will now be made to the embodiment illustrated in the drawing and specific language will be used to describe the same. It will nevertheless be understood that no limitation of the scope of the invention is thereby intended, it being understood that the invention is defined by the appended claims and their legal equivalents; therefore any alterations and further modifications in the illustrated methods, and further applications of the principles of the invention as described and illustrated herein, shall be afforded the broadest protection provided by law.

Referring now to FIG. 1, there is illustrated game board 10. For convenience of carriage and storage, game board 10 may be provided in portions such as rectangular halves 12 which are joined together longitudinally at transversely disposed hinge 14 to form a single rectangular playing surface 16. The surface 16 of game board 10 is divided into seven elongate rectangular shaped playing spaces, each space bearing symbols (preferably at least two) identifying the same, as follows:

1—S—Solidarity
2—E—Explanation
   Cp—Compliance
3—R—Request
4—C—Challenge
5—A—Avoidance
6—M—Making Points Each of the above identified playing spaces represents one of seven mutually exclusive and exhaustive behavior types in which players responses are categorized. Preferably, and as depicted in this embodiment, the playing spaces are sequenced so that each playing space corresponds in position to a response category that functions on an increased or decreased level of emotional distance in accord with the playing space sequence, so as to form a gradient of emotional distance that is an ordinal variable. The value of this variable is useful in measuring (a) the emotional distance between game players' responses, and (b) cognitive differences between players' perspectives regarding the situation they are faced with.

The ordinal variable of emotional distance includes behaviors that function on different levels. The variable of "emotional distance" measures the degree to which people feel emotionally close or distant from one another. This emotional state can be externally measured by categorization of a response provided as a result of querying two or more individuals with regard to a set of social situations and asking for each of the individuals to select a preferred response from a plurality of possible responses. Then, behavior types characterized by the various responses obtained are compared with respect to a scale in which all possible behavior types being characterized have been categorized. Most simply, emotional distance can be described by behavior categories of IN-FACE or OUT-OF FACE. Behavior in SOLIDARITY is IN-FACE, and all other behavior categories are OUT-OF-FACE. More preferably, an emotional distance can be described on at least three different levels: (i) SOLIDARITY, (ii) NEGOTIATION, and (iii) NON COMPLIANCE. SOLIDARITY ("S"), indicates no measurable distance between the perspectives of the players and thereby no measurable emotional distance between the responses of the players, concerning the situation they are faced with.

NEGOTIATION includes three sub-categories of behavior types: (i) EXPLANATION ("E"), which expresses the lowest level of emotional distance between players; (ii) COMPLIANCE ("Cp"), which expresses an increased level of emotional distance; and (iii) REQUEST ("R"), which expresses a level of emotional distance that is greater than that expressed by COMPLIANCE.

NON-COMPLIANCE includes three sub-categories of behavior types: (i) CHALLENGE ("C"), which expresses more emotional distance than REQUEST; (ii) AVOIDANCE ("A"), which expresses more emotional distance than CHALLENGE; and (iii) MAKING POINTS ("M"), which indicates a greater level of emotional distance between players than any of the other behavioral type categories. The latter category, MAKING POINTS, also includes a "PUT-DOWN", as well as a range of behavior from rude assertiveness to criminal action. Thus, the game board provides a spatial indicator of the location of players board markers, thereby allowing the emotional distance between players to be measured and players' performance to be scored. The boundaries between the seven behavior types in which responses are categorized are defined according to how each particular category of response functions during social interaction. The differentiation between the seven response categories, and a method for determining the proper category of a given response, are described in greater detail below in the discussion regarding the RESPONSE CODING CHART.

To initiate game play for game(i), the "BE YOURSELF™" game, each player receives one board marker 20 that bears a number that indicates the playing order of the players and is movable on the game board. I prefer a round marker 20 that is about one (1.0) inch in diameter and one half (0.5) inch thick, when using a game board 10 with dimensions of about eleven (11) inches by seventeen (17) inches.

Figure 4:
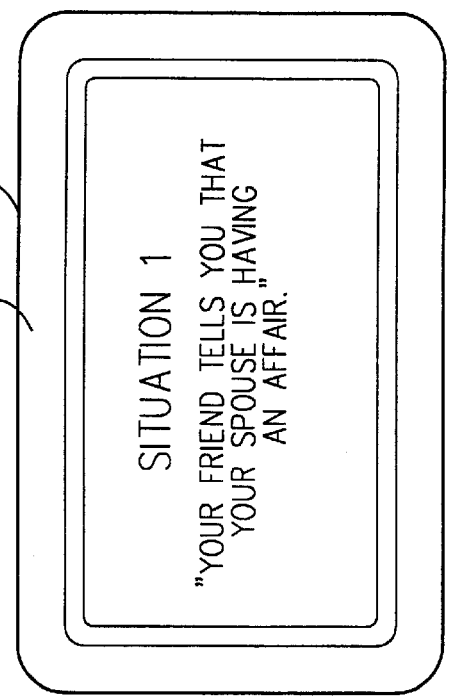
FIG. 4 depicts the reverse side of a game card.
Figure 2:
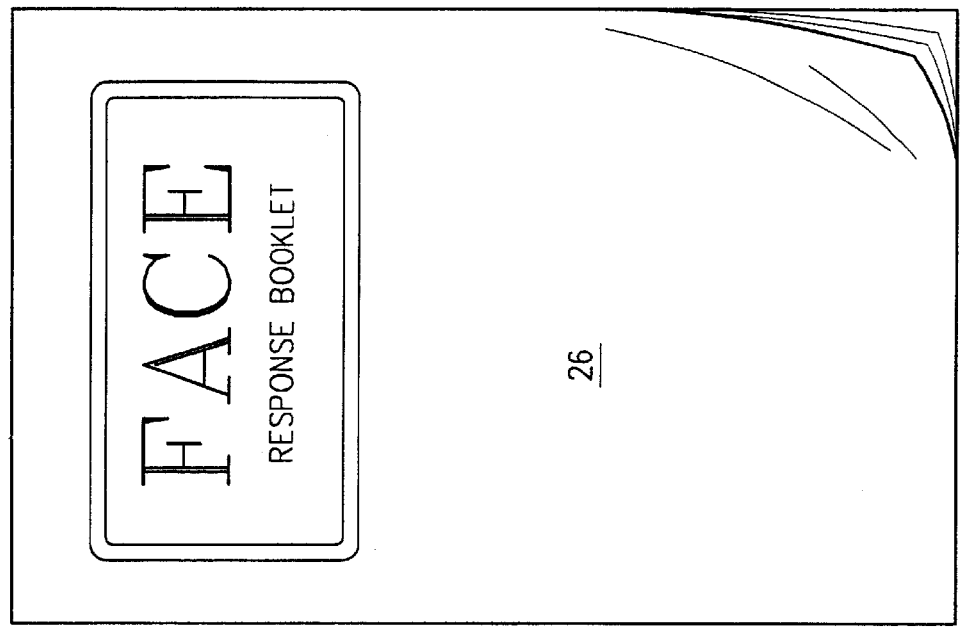
FIG. 2. depicts a response booklet for use in coding responses to particular situations.

The player with board marker number one $20_1$ will draw the first situation card 22 (See FIG. 3) which on the reverse side bears a "SITUATION NUMBER" (See FIG. 4, which shows the reverse side 24 of the situation card 22 revealing a "SITUATION 1") that corresponds to a numbered set of RESPONSE OPTIONS in RESPONSE BOOKLET 26 (shown in FIG. 2). That player will then read aloud the situation posited by the situation card 22. For example, in FIG. 4, a SITUATION 1 is shown, and the player holding marker $20_1$ would read the situation posed, namely, "Your friend tells you that your spouse is having an affair".

As noted above, each SITUATION NUMBER corresponds to a set of RESPONSE OPTIONS listed in the RESPONSE BOOKLET 26. As noted, each of the possible responses is classified by behavior category according to the seven categories discussed above, which categories also correspond to the seven playing spaces on the playing board 10. For SITUATION 1, the RESPONSE OPTIONS 1 include the following possible responses:

(1) "I think you should mind your own business," coded "M;"
(2) "Are you certain," coded "R;"
(3) "We have an open marriage," coded "E;"
(4) "I think you're right," coded "S;"
(5) "let's talk about something else" coded "A;" and
(6) "Other."

Figure 5:
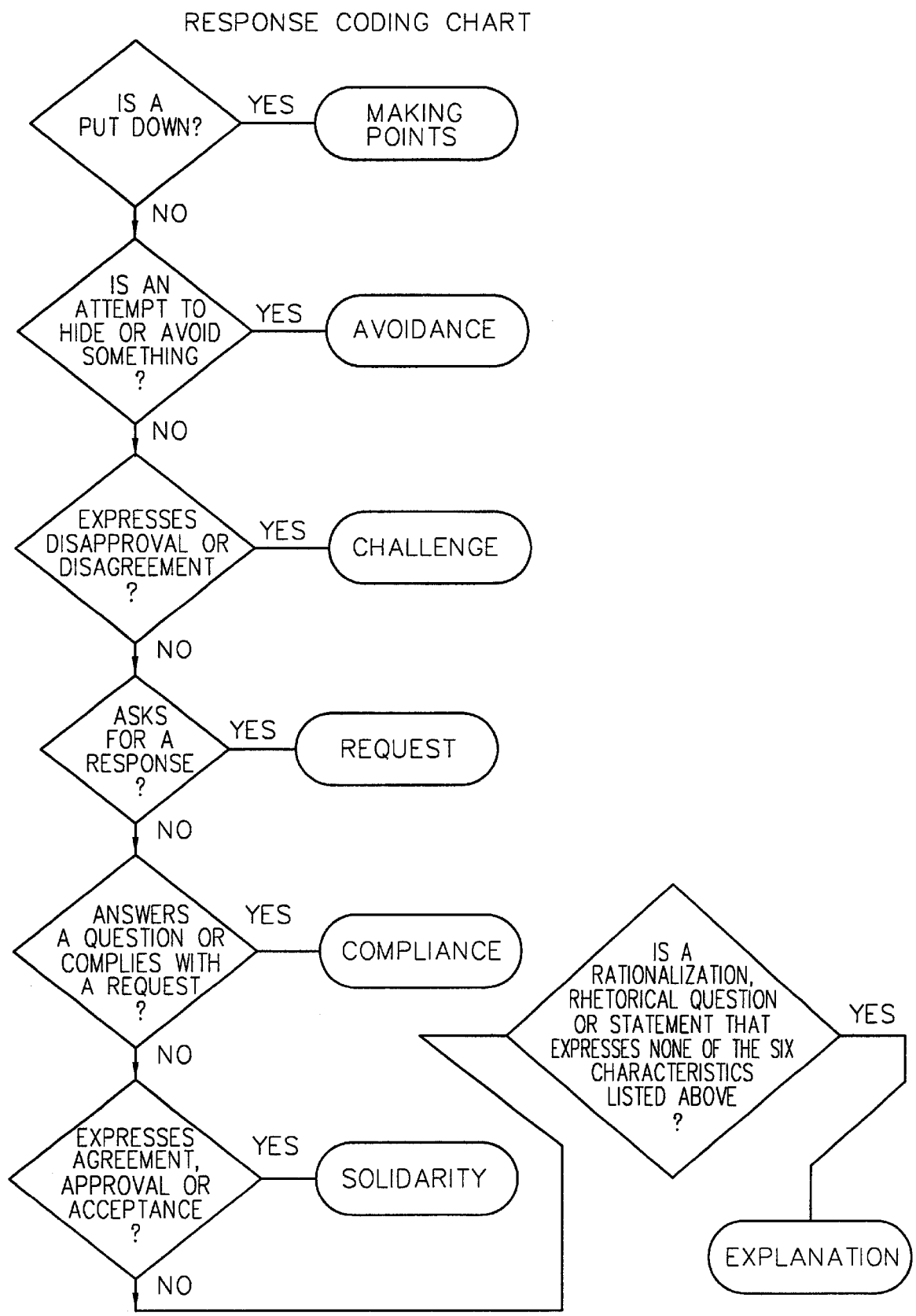
FIG. 5 provides a response coding chart.

Each player will then read the set of RESPONSE OPTIONS 1, silently, to his or her self. If the player finds an appropriate response, i.e. for game(i), a response that he or she would actually make in the given the situation, then he/she will enter the code that follows the RESPONSE OPTION onto the CODE line 30 of score sheet 32, as shown in FIGS. 6A and 6B. For game (ii), the "BE THE OTHER™" game, an appropriate response would be one that the player thinks his or her roletake partner would actually make in the given situation. Then, he/she will enter the code that follows the RESPONSE OPTION on the CODE line 72 of score sheet 70, as shown in FIG. 7. If none of the precoded response options seem to be appropriate, i.e., none is the type of response that the player would ordinarily make for game(i), or is not the type of response that the player thinks his or her roletake partner would actually make in the given situation for game (ii), he or she may create his or her own response, record it on the RESPONSE line 34 of the score sheet 32, or on RESPONSE line 71 of score sheet 70 for game (ii). Then, the player must categorize the just created response by co ding it. This is accomplished by asking the questions shown on the RESPONSE CODING CHART set forth in FIG. 5. The evaluation of the response is done by evaluating whether or not the player's response is:

1) a put down? If yes, it is M for Making Points. If no, is it:
2) an attempt to hide or avoid something? If yes, it is A for Avoidance. If no, is it:
3) an expression of disapproval or disagreement? If yes, it is C for Challenge. If no, is it:
4) a request for a response? If yes, it is R for Request. If no, is it:
5) a polite response or compliance to a request? If yes, it is Cp for Compliance. If no, is it:
6) an agreement, approval, or acceptance? If yes, it is S for Solidarity. If no then it is:
7) a believable statement, rationalization or rhetorical question that communicates information? If so, it is coded E for Explanation.

The each player will then enter the code of his response on the corresponding CODE line 30 of his score sheet 32 or CODE line 72 of his score sheet 70, for game (ii).

As soon as all players have recorded their response codes in line 30 of their score sheets 32 or line 72 of score sheet 70, each player will move his board marker $20_1$, $20_2$, $20_3$, and $20_4$ to the playing space that bears his or her response code for that play. For example, if the response code of player 1 is S for SOLIDARITY, then the player will move board marker $20_1$ to the playing space marked S for SOLIDARITY.

Each player whose board marker 20 is on the same playing space as the majority of players is awarded one "FACE POINT" chip 40, also known as a "ROLE POINT". Each player whose board marker 20 is on any of the other coded playing space categories will receive a ONE DISTANCE POINT chip 42, also known as a "ROLE DISTANCE POINT", for each space that separates his board marker 20 from the board markers of the majority of players.

The definition of the majority which is actually utilized will depend upon the number of players. In the case of one player for game(i), that individual can compare his or her responses against the corresponding codes of a GAME PROFILE made up of the median codes of past game players, to establish the majority. Those skilled in the art to which this invention is directed will recognize that a variety of profiles can be created for different situations of game use, for different social characteristics of the players, and for differing social settings. Table I provides a typical GAME PROFILE for one type of user.

In the case of two players for games(i) and (ii), a majority occurs when both players' board markers are on the same playing space. When their board markers are located on different playing spaces, each player will receive ONE DISTANCE POINT chip 42 for every playing space that separates his board marker from the other player's board marker. A unique situation occurs in the case of two players, since both players achieve the same score. This result simply underscores the equal responsibility that two individuals share for the relationship between them.

When there are more than two players a majority occurs on the playing space with the most board markers placed thereon. However, when there is no majority, a corresponding code from a GAME PROFILE can be used to establish a majority.

The play is completed when each player has received game chips 40 and 42 that represent the proximity of his board marker to that of the majority, in terms of playing spaces, and each player has entered the number of DISTANCE POINT chips or FACE POINT chips for that play in line 31 or 33 of score sheet 32, for game(i) or in lines 73 or 74 of score sheet 70 for game (ii). Player number one will then place the first situation card face down on the bottom of the deck of SITUATION CARDS 22. Next, the player with board marker number 2 will repeat the just described performance of player number 1, and all players repeat the just described process of identifying a response, coding the same, moving board markers, and awarding FACE POINTS 40 and DISTANCE POINTS 42. For convenience and to minimize the number of chips that have to be handled during play, FIVE FACE POINT chips 44 and FIVE DISTANCE POINT chips 46 may also be provided. Play continues in this manner until the deck of situation cards has been exhausted.

At the end of the game process, each player will count the total number of points represented by his FACE POINT chips 40 and 44, and by his DISTANCE POINT chips 42 and 46, and record the totals on the reverse side 50 of his score sheet 32 in the space provided (see FIG. 6B) for game(i), or on his score sheet 70 in the space 77 provided for game (ii) (see FIG. 7).

TABLE I

| GAME PROFILE | |
|---|---|
| PROFILE 1: | SOCIAL CHARACTERISTICS |
| Sex: | 2 Males, 2 Females |
| Age: | Under 25 |
| Family Annual Income: | $20,000–$34,999 |
| Race: | Caucasian |
| Marital Status: | Never Married |
| Education: | Some College |

| RESPONSE CODE MEDIANS: | | | | |
|---|---|---|---|---|
| 1. E | 6. S | 11. C | 16. C | 21. R |
| 2. Cp | 7. C | 12. S | 17. M | 22. C |
| 3. E | 8. C | 13. E | 18. C | 23. C |
| 4. C | 9. Cp | 14. C | 19. R | 24. R |
| 5. Cp | 10. S | 15. S | 20. A | 25. Cp |

The total face points indicate the number of times that a player took the role of the majority, when dealing with the situations provided by the game. The total distance points indicate the emotional difference, i.e., difference in emotional intensity between the responses of the majority and the responses of the individual. In game(i) the extent to which a player is a winner is the decision of the player. It is up to each individual player to decide if the distance symbolized by the DISTANCE POINTS is good or bad. Winning is to have your distance point scores represent who you think you are and what you do in relationship to the other game players. At the end of game (ii) each player will exchange his or her score sheet from game(i) with his or her role partner so that the actual response codes from game one can be entered into column 75 ("Role Response Codes") of score sheet 70 (see FIG. 7). Each player will then record his or her "Role Distance Points" in column 76 by comparing the "CODE" column 72 with the "Role Response Codes" column 75 to find the distance in terms of the categories of the game board. The winner of game (ii) is the player with the smallest total number of "Role Distance Points".

For completeness, it may be helpful to review how the method of evaluating the emotional distance between individuals is determined during implementation of the game playing process. To begin the "FACE(tm)" game playing process, a deck is formed from an ordered series of SITUATION CARDS 22. A RESPONSE BOOKLET 26, a SCORE SHEET 32, for game (i) or a SCORE SHEET 70 for game (ii), a RESPONSE CODING CHART (FIG. 5) and a BOARD MARKER 20 is allocated to each player. The player who decides to be banker will take control of the FACE POINT chips 40 and 44, the DISTANCE POINT chips 42 and 46, and a GAME PROFILE for game (i). The player with BOARD MARKER 20 number one (201) will take the first SITUATION CARD 22, read it aloud to the other players and place it face up on the GAME BOARD 10. This SITUATION CARD 22 sets forth the situation that all of the players are faced with for that play. Each player then scans the coded responses in his RESPONSE BOOKLET 26. If he finds an appropriate response, then he will record the code of that response in the corresponding CODE 30 space on his SCORE SHEET 32 for game(i) or the corresponding CODE 72 space on his SCORE SHEET 70 for game (ii). If he does not find an appropriate response then he will create his own response, record it on the RESPONSE LINE 34 provided on his SCORE SHEET 32 or on the RESPONSE LINE 71 of his SCORE SHEET 70 for game (ii). The response must be coded using the RESPONSE CODING CHART of FIG. 5. The response code must be recorded on the CODE 30 space on his SCORE SHEET 32 for game(i) or on the CODE 72 space on his SCORE SHEET 70 for game (ii).

After all players have recorded their RESPONSE CODES 30 on their SCORE SHEETS 32 for game(i) or on their SCORE SHEETS 70 for game (ii), each player will move his BOARD MARKER 20 to the playing space that bears the same CODE 30 for game (i) or CODE 72 for game (ii) as his response. Players must not discuss their responses until after their BOARD MARKERS 20 have been moved, their DISTANCE SCORES and FACE SCORES have been recorded on SCORE SHEETS 32 for game(i) and SCORE SHEETS 70 for game (ii) and the FACE POINT chips 40 and 44 and the DISTANCE POINT chips 42 and 46 have been obtained for a particular play. A player whose BOARD MARKER 20 is on the same playing space as the majority will receive one FACE POINT chip 40. A player whose BOARD MARKER 20 is on any of the other playing spaces will receive ONE DISTANCE POINT chip 42 for each playing space that separates his BOARD MARKER from the board marker(s) of the majority. Each player will then record either the number of DISTANCE POINT chips 42 and 46 or FACE POINT chips 40 and 44 (earned for that play) in space 31 or 33 for game (i), or in space 73 or 74 for game (ii). Player number one will then place the SITUATION CARD 22 face down under the deck of SITUATION CARDS.

Each player, in turn, will repeat this process until the deck of SITUATION CARDS is exhausted. Each player will then count his FACE POINT chips 40 and 44, and his DISTANCE POINT chips 42 and 46, and record the totals on the back of his score sheet on the lines provided on the reverse side 50 of score sheet 32 for game(i), and on line 77 on SCORE SHEET 70 for game (ii). Players who are not pleased with their distance scores from game (i), the BE YOURSELF™ game, will want to play game (ii) BE THE OTHER™, to learn how to take the role of the other, or game (iii) CREATE THE OTHER™ to experience the link between emotion and the expression of that emotion in terms of behavior function, or the DIPLOMACY™ game, to learn how to negotiate emotional distances in relationships that are important to them.

To initiate game (iii), each player will role the die 48 (see FIG. 1) to determine a playing order. Then, player one will take the first SITUATION CARD 22 read it aloud to the other players, and place the SITUATION CARD 22 face up on the GAME BOARD 10. Player one will roll the die and try to create a response to the situation that functions in the same way as the category of behavior on the game board that bears the same number as the number on the die. For example, if the die displays a one, then the player will try to create a response from the "1" SOLIDARITY category, write it on his or her SCORE SHEET 80 in space 81 (see FIG. 8), record the CODE in space 82, and read the response aloud. The other players will listen to the response, record it on their SCORE SHEETS 80, in space 81, or use the RESPONSE CODING CHART to code the response and enter the response in CODE space 82. Then, players either agree that player one has created a response from the SOLIDARITY category, or use the information recorded on their RESPONSE CODING CHART to explain why the response cannot be categorized as SOLIDARITY. Player one will take one DISTANCE POINT chip 42 when the other players do not agree that he or she has created the correct response, and will take one FACE POINT 40 chip when the others can agree that he or she has created the correct response. Player one will then place the SITUATION CARD 22 face down under the deck of SITUATION CARDS. Each player, in turn, will repeat this process until the deck of SITUATION CARDS is exhausted. Each player will then count his FACE POINT chips and his DISTANCE POINT chips and record the totals on his SCORE SHEET 80, on the lines provided. The winner, i.e., the player with the lowest emotional distance, is the player with the least Distance Points.

To initiate the Diplomacy™ game, (i.e., a task completion activity) from two to four participants will select a task to complete, based upon their scores for game(i) (see the "Task Selection Chart" FIG. 6B). For example, Task #2 is the development of a slogan for a poster about abortion to be carried in turns by the participants in an upcoming "Abortion Demonstration". Twenty minutes is allowed for this activity. A poster board and set of felt markers are provided. Each participant will be provided a Response Coding Chart (See FIG. 5) and instructed to respond to the other group members using only responses from the SOLIDARITY and NEGOTIATION categories, during the completion of that task, here, TASK #2. Each player must write down all of his responses on the RESPONSES space 61 on SCORE SHEET 60 (see FIG. 9A). Then at the end of the time allowed for the task, each player will be asked to exchange score sheets and to record a code for each of the other players' responses. When the score sheets have returned from being coded by the other players, each player will record the "Median Codes" in column 66, find the "Distant Points" 67 by counting the number of behavior categories between REQUEST (the last category of NEGOTIATION) and any median codes that belong to the NON-COMPLIANT categories. Each player will then count his or her "Distance Points" and record the total IN SPACE 68 (see FIG. 9B). The DIPLOMACY™ game score evaluates the emotional distance between the player's intention to use only diplomatic responses and the player's demonstrated ability to do so. The winner in the DIPLOMACY™ game is the player with the smallest number of total "Distant Points".

Figure 10:
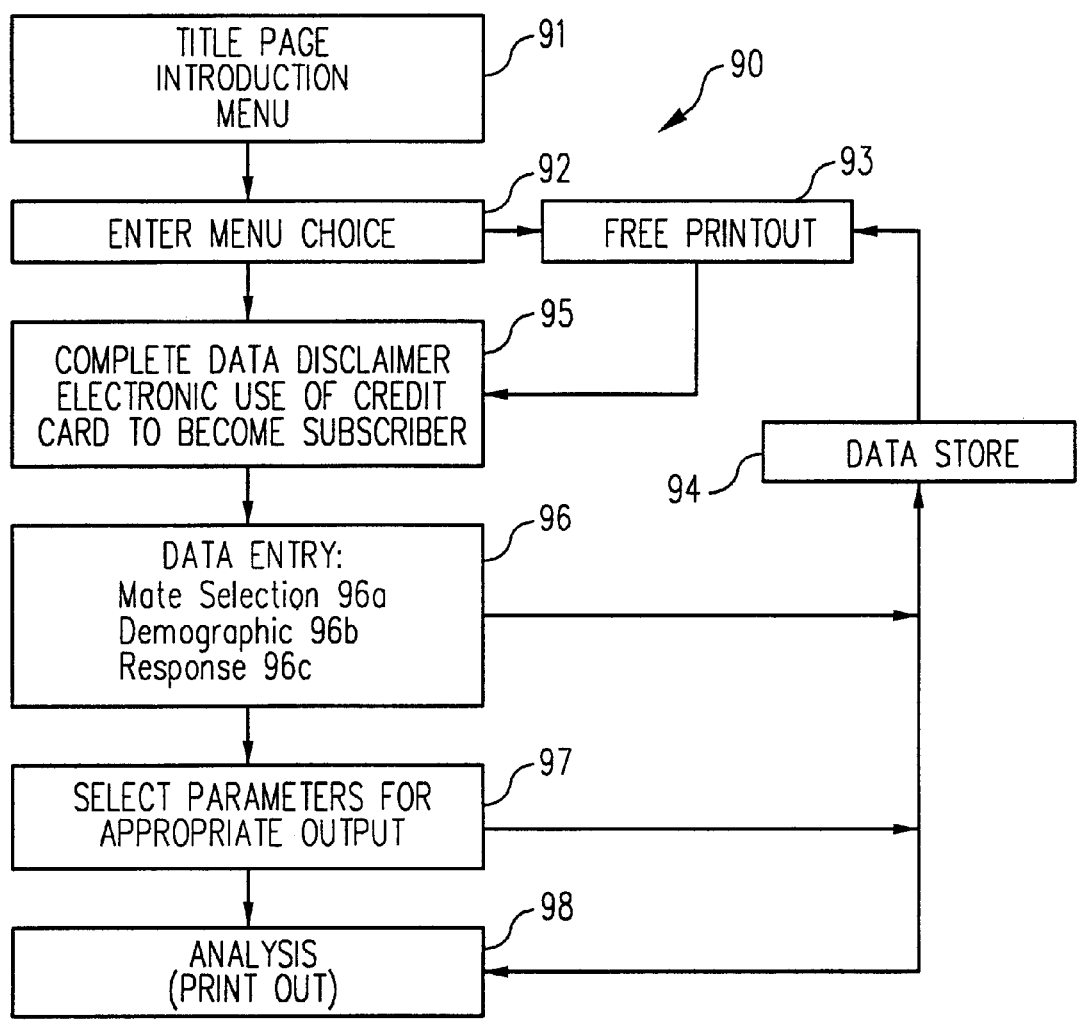
FIG. 10 provides a flow chart.

The Internet based business described herein is a fully integrated on-line data processing system that records data, analyzes data, and provides relational assessments and recommendations for users. In particular, the data processing system provides a menu 90 (see FIG. 10) of questions (see FIG. 11) that circumscribe the type of information subscribers could expect to receive, and offers an output, in the form of a screen display or printout 93 as a free example, given a particular choice at menu 92. The user may sign up electronically using a credit card at signup step 95. Subscribers to the "A" portion of the database would enter mate selection data 96a at data entry step 96. Subscribers to the "A", "B", "C", "D", "E", and "F", portions of the database would enter their demographic 96b and response data 96c at the data entry step 96. In the next step, subscribers to the "A", "B", "C", "D", "E", "F", and "G" portions of the database would select appropriate parameters 97 for sorting the data to answer the menu questions selected. The data processing system determines the emotional distance between appropriate members of the database and provides an output analysis 98 such as printout that is responsive to specific menu questions selected by the subscriber (see FIG. 11).

In the game portion, players who are not pleased with their game scores can play additional games (up to and including all four games described herein) to gain a better understanding of the rules of the game that people play during social interaction. It is interesting to replay each game in an attempt to achieve a different game score. The situations in which the face or role distance occurs can be identified by comparing the codes for each situation, among the various players' score sheets.

The four games described herein operationalize a unified theory of social psychology which is useful on both micro and macro levels. The disclosed method for measuring the emotional distance between individuals in a preselected social situation, as may be represented by the categorization and profiling of players responses to game cards or the like, provides a tool for the prediction of emotional distance between individuals in specific human interaction situations. It is a feature of the present invention and the games described to implement the invention that descriptive, discrete, and categorically complete behavior types are established in order to create a methodology for measurement of the emotional distance between individuals. The results of the games can be used to predict productivity in workgroups, as well as the tendency of workgroup members to like one another, as a result of their interaction, when the task to be performed by the workgroup requires them to deal with an emotionally distancing issue which is addressed by the specific game. When members of groups engage in more NON-COMPLIANT behavior, their productivity tends to fall, this tendency is measured by the method and game process described herein. This result is in agreement with everyday experience; those groups which tend to argue will likely get less done. The method used by the game can also be used to identify patterns of dominance in group interaction. Dominance is revealed by the number of COMPLI-ANCE responses a particular group member receives when compared to the number of COMPLIANCE responses received by the other group members.

It will be understood that variations of the game processes and my method of compiling and utilizing information stored in various database portions can be made without departing from the teachings and principles described herein. Also, counting arrangements other than the means described above can be used for scoring the psycho-social game process. For example, a computerized embodiment of the invention could be programmed to allow player access, accumulate the scores, compare one players' scores with other player's scores, generate game profiles, compare players' scores with profiles, printout an analysis of these results for each player's responses and accumulate a database.

Also, it will be understood that the method and game process taught herein, in its entirety as well as in portions thereof, may be useful in a wide variety of applications, examples of which are set forth below.

EXAMPLE I

Behavioral Science

Behavioral scientists may use the behavior response categories and coding process taught herein to relate such variables as productivity, dominance, self-esteem. For example, "liking," i.e., how much people tend to like one another as a result of their interaction, may be examined. Also, use of the response categories may lead to evaluations of and classification of particular proportions of specific categories of observable behavior.

EXAMPLE II

Industry Productivity

Industry may use the method and/or the game taught herein to improve the productivity of work groups. That is, the emotional distance amongst workgroup members can be evaluated, and, if desirable, workgroup selection can be managed so as to minimize the likelihood of friction generated by emotionally distant members (i.e., high NON-COMPLIANCE COMPLIANCE results from DISAGREEMENT, AVOIDANCE, and MAKING POINTS).

EXAMPLE III

Safety

Employers such as airlines may use the methods and/or games taught herein to improve the safety of selected crew pairings, such as cockpit crew members. That is made possible because the emotional distance between potential crew members can be evaluated, and, if necessary or desirable, crew selection can be managed so as to minimize the possibility of friction, or undesirable dominance of one member over another, so as to minimize crew selections containing undesirably emotionally distant members.

EXAMPLE IV

Law

Trial lawyers may use the behavior categorization system for jury selection, so as to attempt to pick individuals whose answers would predict minimal emotional distance from the desired result. Also, the method may be useful for negotiators in dispute resolution, in assisting in understanding the behavior exhibited, and therefor providing a basis for addressing the differences between parties.

EXAMPLE V

Education

Educators may use the game for teaching human relations. The game may be of particular interest to students of such subjects as social science, law, medicine, social services, diplomacy, sales, advertising and parenting.

This invention may be embodied in still other specific forms without departing from the spirit or essential characteristics thereof. It will be appreciated by those skilled in the art to which this invention pertains that the methods illustrated herein may be embodied in a machine implemented method susceptible of execution on a data processor without departing from the scope and spirit of the claimed invention. Further, it can be readily appreciated that the number of categories utilized may be varied upward or downward. For example, only the three categories of SOLIDARITY, NEGOTIATION, and NON-COMPLIANT behavior may be used to some advantage. Also, use of simply two categories, IN-FACE and OUT-OF-FACE, will be useful in other situations. Likewise, a number of categories in excess of seven may be utilized. Alternatively, subdivisions of the seven categories (or other chosen number of categories) provided may be utilized to further define degrees of emotional distance between individuals. And, although the order of categories illustrated provides an incremental scale of emotional distance between individuals, the categories could be otherwise ordered and the mathematical computations performed to achieve a similar measurement of emotional distance between individuals, without varying from the teachings herein. The present embodiments are therefore to be considered in all respects as illustrative and not restrictive, the scope of the invention being indicated by the appended claims rather than by the foregoing description. All changes which come within the meaning and range of the claims and their legal equivalents, are therefore intended to be embraced therein.

I claim:

1. A method for collecting, processing, and output of data to provide a measurement of the emotional distance between two or more preselected individuals in one or more preselected social situations, each of said preselected individuals being subscribers to a data service, said method comprising:
   (a) a computerized database file for input, storage, and output of one or more of the following:
      (i) personal data characterizing each one of a plurality of subscribers to said data service,
      (ii) demographic data of each one of a plurality of subscribers to said data service,
      (iii) ideal personal data characterizing a desirable mate for at least one subscriber to said data service,
      (iv) response data characterizing preferred responses by each one of a plurality of subscribers to one or more hypothetical situations,
      (v) response data characterizing the attitude of each one of a plurality of subscribers to one or more specific issues,
   (b) selecting one or more questions directed to any one or more of items (a)(i) through (a)(v) for presentation to a subscriber via a tangible medium of expression;
   (c) presenting via a tangible medium of expression said one or more questions to each one of a plurality of subscribers,
   (d) presenting each one of said plurality of subscribers with a plurality of possible responses to each of said one or more questions;
   (e) recording in said database the actual response provided by each subscriber to each of said one ore more questions, and wherein each actual response is recorded in a preselected behavior type category;
   (f) comparing said behavior types by measuring the distance, on an ordinal scale including two or more preselected behavior type categories, between any of said two or more preselected behavior type categories into which the answers provided by each of said individuals in actual response to said one or more questions has been recorded.

2. The method of claim 1, wherein the step of presenting, via a tangible medium of expression, said one or more questions is accomplished by
   (a) recording said questions in a general purpose computer with database, and
   (b) presenting to each one of a plurality of database subscribers, via remotely linked computer display, such recording.

3. The method of claim 1, wherein the step of presenting, via a tangible medium of expression, a plurality of possible responses to said one or more questions is accomplished by
   (a) recording said possible responses in a general purpose computer with database, and
   (b) presenting to each one of a plurality of database subscribers, via remotely linked computer display, such recording.

4. The method of claim 1, wherein the step of recording, in said database the actual response provided by each one of a plurality of database subscribers by a preselected behavior type, is accomplished by recording in a general purpose computer with data base.

5. The method of claim 1, wherein the step of comparing said behavior type categories by measuring the distance, on an ordinal scale including two or more preselected behavior type categories, between any of said two or more preselected behavior type categories into which the answers provided by each one of a plurality of subscribers in actual response to said questions has been recorded, is accomplished mathematical calculations performed on a general purpose computer, using data stored in a data base program.

6. The method of claim 1, wherein said preselected behavior type categories comprise
   (a) IN-FACE behavior, and
   (b) OUT-OF-FACE behavior.

7. The method of claim 1, wherein said possible responses comprise at least three behavior type categories.

8. The method of claim 7, wherein said at least three behavior type categories comprise behavior type categories:
   (a) SOLIDARITY,
   (b) NEGOTIATION, and
   (c) NON-COMPLIANT behavior.

9. The method of claim 8, wherein said NEGOTIATION behavior type category further comprises the behavior type categorized as EXPLANATION.

10. The method of claim 5 or claim 8, wherein said behavior type category identified as NEGOTIATION further comprises the behavior type categorized as COMPLIANCE.

11. The method of claim 8, or claim 9, or claim 10, wherein said NEGOTIATION behavior type category further comprises the behavior type categorized as a REQUEST.

12. The method of claim 8, wherein said behavior type categorized as NON-COMPLIANT further comprises the behavior type categorized as CHALLENGE.

13. The method of claim 8 or claim 12, wherein said NON-COMPLIANT behavior type further comprises the behavior type categorized as AVOIDANCE.

14. The method of claim 8 or claim 12 or claim 13, wherein said NON-COMPLIANT behavior type further comprises the behavior type categorized as MAKING POINTS.

15. A method for collecting, processing, and output of data to provide a measurement of the emotional distance between two or more preselected individuals in one or more preselected social situations, each of said preselected individuals being subscribers to a data service, said method comprising:
   (a) a computerized database file for input, storage, and output of descriptions of one or more social situations for presentation to each one of said plurality of subscribers to said data service via remote access to a computer display;
   (b) presenting via said computer display said description of said one or more social situations to at least two of said plurality of subscribers, and then
   (c) presenting each of said at least two of said plurality of subscribers with a plurality of possible responses to each of said one or more social situations;
   (d) recording in said database the actual response provided by each one of said plurality of subscribers to said one or more social situations, wherein each actual response to each of said one or more social situations is selected from said plurality of possible responses to each of said one or more social situations, and wherein each actual response is recorded in a preselected behavior type category;
   (e) comparing via general purpose computer said behavior types by measuring the distance, on an ordinal scale including at least seven preselected behavior type categories, between any of said at least seven preselected behavior type categories into which the answers provided by each one of said plurality of subscribers in actual response to said one or more social situations has been recorded, and
   (f) wherein said at least seven behavior type categories comprise a set of at least the following behavior type categories:
      (i) SOLIDARITY;
      (ii) EXPLANATION;
      (iii) COMPLIANCE;
      (iv) a REQUEST;
      (v) a CHALLENGE;
      (vi) AVOIDANCE; and
      (vii) MAKING POINTS.

16. The method of claim 15, wherein the step of presenting said description of said one or more social situations is accomplished by
   (a) presentation via remote computer display connected to a general purpose computer with database, and
   (b) showing such recording to each one of said plurality of subscribers.

17. The method of claim 15, wherein the step of presenting a plurality of possible responses to one or more social situations to each one of a plurality of subscribers is accomplished by
   (a) recording said description of said possible in a general purpose computer with database, and
   (b) showing such recording to each one of said plurality of subscribers.

18. The method of claim 15, wherein the step of recording the actual response provided by each one of said plurality of subscribers by a preselected behavior type, is accomplished by recording said response in a general purpose computer with database.

19. The method as described in claim 15, wherein a value is assigned to each of said behavior type categories along an ordinal variable, said value determinant of the sequence and relation of each of said behavior type categories one to another, so as to establish a distance value between said behavior type categories, each from the other.

20. The method of claim 19, wherein the step of comparing said behavior type categories by measuring the distance, on an ordinal scale including two or more preselected behavior type categories, between any of said two or more preselected behavior type categories into which the answers provided by each one of said plurality of subscribers in actual response to said one or more social situations has been recorded, is accomplished by mathematical calculations performed on a general purpose computer, using data stored in a database program.

21. The method as described in claim 20, further comprising analyzing the distance between said behavior type categories of said preferred responses, of each one of said plurality of database subscribers, each one from the other, to each preselected social situation.

22. The method as set forth in claim 21, further comprising analyzing the median value of the behavior type categories selected in response to each preselected social situation, for a selected plurality of subscribers.

23. The method as set forth in claim 22, wherein each of the behavior type categories which are identified are ordered with respect to the other, in a set of variables comprising the preselected behavior type categories, so that each succeeding behavior type category along an ordinal direction corresponds to a behavior type category that functions on an increased level of emotional distance, so as to form a gradient between behavior type categories along an ordinal variable, so that emotional distance is measured by determining the distance between the location of said behavior type categories along said ordinal variable.

24. A process for measuring the emotional distance between two or more individuals in a group, to a set of preselected social situations, wherein said process comprises the steps of:
   (a) selecting a description of one or more social situations for presentation in a tangible medium of expression;
   (b) presenting via a tangible medium of expression said description of said one or more social situations to two or more members of a group of members, and then (c) presenting each of such two or more preselected members of a group of members with a plurality of possible responses to each of said one or more social situations;

(d) recording in a tangible medium of expression the actual response provided by each of such two or more members of a group of members to each of said one or more social situations, wherein each actual response to each of said one or more social situations is selected from said plurality of possible responses to each of said one or more social situations, and wherein each actual response is recorded in a preselected behavior type category;

(e) comparing said behavior types by measuring the distance between said categorized behavior types, each of which categorized behavior types represent said preferred responses from each of such members of said group of members, on an ordinal scale;

(f) wherein said at least seven categories are provided for said behavior type categories, and wherein said behavior type categories comprise a set of at least the following:
(i) SOLIDARITY;
(ii) EXPLANATION;
(iii) COMPLIANCE;
(iv) a REQUEST;
(v) a CHALLENGE;
(vi) AVOIDANCE; and
(vii) MAKING POINTS.

25. A process for measuring the emotional distance between two or more individuals in a group, to a set of preselected social situations, wherein said process comprises the steps of:

(a) selecting a description of one or more social situations for presentation in a tangible medium of expression;

(b) presenting via a tangible medium of expression said description of said one or more social situations to two or more members of a group of members, and then (c) presenting each of such two or more preselected members of a group of members with a plurality of possible responses to each of said one or more social situations;

(d) recording in a tangible medium of expression the actual response provided by each of such two or more members of a group of members to each of said one or more social situations, (e) analyzing each of such actual responses to determine the quality of such responses by categorizing each response to determine a response code, wherein each of said responses are categorized by behavior type and each behavior type corresponds to a response code; and (f) comparing said behavior types by measuring the distance between said categorized behavior types, each of which categorized behavior types represent said preferred responses from each of such members of said group of members, on an ordinal scale;

(g) wherein said at least seven categories are provided for said behavior type categories, and wherein said behavior type categories comprise a set of at least the following:
(i) SOLIDARITY;
(ii) EXPLANATION;
(iii) COMPLIANCE;
(iv) a REQUEST;
(v) a CHALLENGE;
(vi) AVOIDANCE; and
(vii) MAKING POINTS.

26. The method of claim 24 or of claim 25, wherein the process is carried out on a game board having a plurality of playing spaces comprising a set of behavior type categories, said behavior type categories ordered on said board in a graduated relationship so as to represent increasing levels of emotional distance between said possible response choices of said group members, so that the distance between the playing spaces corresponds to the distance between behavior type categories being selected from said possible responses.

27. The method of claim 26, wherein each of said members of said group of members is provided with a board marker for indicating to said group member his/her position on the game board, and wherein the process further comprises the step of moving each group member s board marker to the playing space corresponding to that of said player's preferred response code corresponding to the behavior type category selected by that group member in response to a preselected social situation which is presented.

28. The method of claim 27, wherein the process further comprises awarding one FACE POINT chip to each preselected group member whose board marker position corresponds to the position on said game board of a majority of the board markers of all of said group members.

29. The method of claim 28, wherein the process further comprises awarding one DISTANCE POINT chip to each preselected group member for each space on said board by which that group member's board marker position is located away from the board marker position of the majority of group members, so that the DISTANCE POINT chip represents the emotional distance of a selected group member from the position of the majority of the group members.

30. The method of claim 29, wherein each DISTANCE POINT chip corresponds with one playing space of distance between (a) the behavior type category selected by a preselected group member as indicated by his/her response code, and represented by the location of his/her board marker position, and (b) the behavior type category selected by the majority of group members, as indicated by the response code of the majority of group members, and as represented by the location of board marker positions of the majority of group members.

31. The method of claim 30, wherein each FACE POINT chip awarded corresponds with agreement between (a) the response code of the preselected group member and (b) the response code of the majority of group members game players, (c) so that there is a common location between the board marker position of a preselected game player and the board marker positions of the majority of group members.

32. The method of claim 31, wherein said game board surface comprises seven playing spaces, and wherein each of said seven playing spaces corresponds to a preselected behavior type category.

33. The method of claim 32, wherein each playing space contains a symbol indicator that corresponds to a preselected behavior type category.

34. The method of claim 24, or claim 25, wherein each behavior type category functions as an indicator of a preselected group member's externally observable response to a preselected social situation, so that by comparison between behavior type categories which are chosen by various individuals amongst group members, an indicia of the emotional distance between various of such group members, when they face the same social situation, can be determined.

35. The method as set forth in claim 34, wherein the said seven playing spaces correspond to a gradient of seven behavior type categories, along which gradient an indicia of emotional distance between preselected game players may be determined.

36. The method as set forth in claim 35 wherein said seven levels of behavior type categories correspond to seven mutually exclusive and exhaustive functional categories of behavior types.

37. The method as set forth in claim 36, wherein said seven playing spaces correspond to the behavior type categories comprising
   (i) SOLIDARITY;
   (ii) EXPLANATION;
   (iii) COMPLIANCE;
   (iv) a REQUEST;
   (v) a CHALLENGE;
   (vi) AVOIDANCE; and
   (vii) MAKING POINTS.

38. The method of claim 37 wherein the number of COMPLIANCE responses received by a preselected group member corresponds with the amount of dominance by that preselected group member, which is externally observed by each of the other of said group members.

39. The method of claim 38, wherein an increase in the NON-COMPLIANT behavior type category response code accumulated by a preselected group member corresponds with a predicted decrease in productivity of group members.

40. The method of claim 39, wherein an increase in the NON COMPLIANT behavior type category response codes accumulated by a preselected group member corresponds to a dislike of said preselected group member amongst other group members.

41. A method for collecting, processing, and output of data to provide a measurement of the emotional distance between two or more preselected individuals in one or more preselected social situations, each of said preselected individuals being subscribers to a data service, said method comprising:
   (a) a computerized database file for input, storage, and output of one or more of the following:
      (i) personal data characterizing each one of a plurality of subscribers to said data service,
      (ii) demographic data of each one of a plurality of subscribers to said data service,
      (iii) ideal personal data characterizing a desirable mate for at least one subscriber to said data service,
      (iv) response data characterizing preferred responses by each one of a plurality of subscribers to one or more hypothetical situations,
      (v) response data characterizing the attitude of each one of a plurality of subscribers to one or more specific issues,
   (b) selecting one or more questions directed to any one or more of items (a)(i) through (a)(v) for presentation to a subscriber;
   (c) presenting said one or more questions to each one of a plurality of subscribers,
   (d) presenting each one of said plurality of subscribers with a plurality of possible responses to each of said one or more questions;
   (e) recording in said database the actual response provided by each subscriber to each of said one or more questions, and wherein each actual response is recorded in a preselected behavior type category;
   (f) comparing said behavior types by measuring the distance, on an ordinal scale including two or more preselected behavior type categories, between any of said two or more preselected behavior type categories into which the answers provided by each of said individuals in actual response to said one or more questions has been recorded.

42. The method of claim 41, wherein the step of presenting said one or more questions is accomplished by
   (a) recording said questions in a general purpose computer with database, and
   (b) presenting to each one of a plurality of database subscribers, via remotely linked computer display, such recording.

43. The method of claim 41, wherein the step of presenting a plurality of possible responses to said one or more questions is accomplished by
   (a) recording said possible responses in a general purpose computer with database, and
   (b) presenting to each one of a plurality of database subscribers, via remotely linked computer display, such recording.

44. The method of claim 41, wherein the step of recording, in said database the actual response provided by each one of a plurality of database subscribers by a preselected behavior type, is accomplished by recording in a general purpose computer with data base.

45. The method of claim 41, wherein the step of comparing said behavior type categories by measuring the distance, on an ordinal scale including two or more preselected behavior type categories, between any of said two or more preselected behavior type categories into which the answers provided by each one of a plurality of subscribers in actual response to said questions has been recorded, is accomplished mathematical calculations performed on a general purpose computer, using data stored in a data base program.

46. The method of claim 41, wherein said preselected behavior type categories comprise
   (a) IN-FACE behavior, and
   (b) OUT-OF-FACE behavior.

47. The method of claim 41, wherein said possible responses comprise at least three behavior type categories.

48. The method of claim 47, wherein said at least three behavior type categories comprise behavior type categories:
   (a) SOLIDARITY,
   (b) NEGOTIATION, and
   (c) NON-COMPLIANT behavior.

49. The method of claim 48, wherein said NEGOTIATION behavior type category further comprises the behavior type categorized as EXPLANATION.

50. The method of claim 45 or claim 48, wherein said behavior type category identified as NEGOTIATION further comprises the behavior type categorized as COMPLIANCE.

51. The method of claim 48, or claim 49, or claim 50, wherein said NEGOTIATION behavior type category further comprises the behavior type categorized as a REQUEST.

52. The method of claim 48, wherein said behavior type categorized as NON-COMPLIANT further comprises the behavior type categorized as CHALLENGE.

53. The method of claim 48, wherein said NON-COMPLIANT behavior type further comprises the behavior type categorized as AVOIDANCE.

54. The method of claim 48 or claim 52 or claim 53, wherein said NON-COMPLIANT behavior type further comprises the behavior type categorized as MAKING POINTS.

55. The method of claim 41, wherein at said two or more behavior type categories comprise a set of at least the following seven behavior type categories:

(i) SOLIDARITY;
(ii) EXPLANATION;
(iii) COMPLIANCE;
(iv) a REQUEST;
(v) a CHALLENGE;
(vi) AVOIDANCE; and
(vii) MAKING POINTS.

* * * * *